United States Patent [19]
Ransford

[11] Patent Number: 4,841,959
[45] Date of Patent: Jun. 27, 1989

[54] SPINAL/SKULL FIXATION DEVICE

[75] Inventor: Andrew O. Ransford, London, England

[73] Assignee: A. W. Showell (Surgicraft) Limited, Redditch, England

[21] Appl. No.: 244,053

[22] Filed: Sep. 13, 1988

[30] Foreign Application Priority Data

Sep. 15, 1987 [GB] United Kingdom ............... 8721661

[51] Int. Cl.$^4$ ............................................. A61F 5/04
[52] U.S. Cl. ........................ 128/192 YM; 128/92 YD
[58] Field of Search ............... 128/92 YE, 92 YD, 68, 128/69, 84 R, 92 YF, 92 YC, 92 YM

[56] References Cited

U.S. PATENT DOCUMENTS

| | | | |
|---|---|---|---|
| 4,573,454 | 3/1986 | Hoffman | 128/69 |
| 4,604,995 | 8/1986 | Stephens et al. | 128/69 |
| 4,686,970 | 8/1987 | Dove et al. | 128/69 |
| 4,773,402 | 9/1988 | Asher et al. | 128/69 |

FOREIGN PATENT DOCUMENTS

| | | | |
|---|---|---|---|
| 261038 | 3/1988 | European Pat. Off. | 128/69 |
| 8702444 | 2/1987 | France . | |
| 1057026 | 11/1983 | U.S.S.R. | 128/92 YD |
| 2198043 | 6/1988 | United Kingdom | 128/68 |

Primary Examiner—Edgar S. Burr
Assistant Examiner—Moshe I. Cohen
Attorney, Agent, or Firm—R. A. Giangiorgi

[57] ABSTRACT

A device for fixation of the skull (15) to adjacent bones (18A ... 18E) of the spine (19) comprises a loop (11) of substantially circular form connecting a pair of legs (12) generally perpendicular to the loop, outward kinks (14) being provided adjacent the junction of the loop and legs, whereby, with the loop secured to the skull by wires (16) and the legs secured to the spine by sublaminae wires (20), wires (20', 20") at both sides of the kinks (14) effect fixation of the skull in relation to the adjacent bones of the spine.

8 Claims, 4 Drawing Sheets

ABSTRACT## SPINAL/SKULL FIXATION DEVICE

This invention relates to a device for fixation of the skull to adjacent bones of the spine for stabilisation of the occipito-cervical area, mainly to stabilise the base of the skull in relation to the neck, e.g., after odontoidectomy with removal of part of the anterior arch of the atlas, which decompression is sometimes required in the rheumatoid patient, in trauma to the occipito-atlantal joints, for fixation of Jefferson fractures (burst fracture of the atlas), after excision of "benign" disease of the cervical vertebrae, (i.e., after vertebrectomy for chordoma, osteoclastoma and hydatid disease, etc.), or in cervical stabilisation for disseminated metastatic disease (i.e., after anterior decompression of the neuraxis).

According to the present invention, a device for fixation of the skull to adjacent bones of the spine comprises biocompatible rod-like material formed in the slope of a loop of substantially circular form connecting a pair of generally parallel legs, with the loop and the legs at their junction lying in planes that are generally perpendicular to each other, and the legs being provided adjacent that junction with outward kinks, whereby, when the loop has been secured to the base of the skull by means of wires (or other strands) passing through holes in the skull and the legs have been secured to adjacent bones of the spine by sublaminate wires (or other strands), wires (or strands) engaged round the legs at both sides of the kinks effect fixation of the skull in relation to the adjacent bones of the spine.

The loop may need a superior concavity to fit the base of the skull; this concavity can be provided and/or modified by the surgeon by means of suitable bending tools, and then the sites of the holes in the skull can be marked. Conveniently, the loop is formed in a flat plane and bent by the surgeon. The neck should be extended to a normal alignment before testing the loop for a good fit.

A normal cervical lordosis is essential and so the legs are preferably formed towards their free ends in a plane curving to the same side as that to which the loop extends from the other ends of the legs. The legs may be elongated so as to be able to continue the fixation segmentally into the dorsal spine if this is indicated as desirable, i.e., for multiple metastaces, and appropriate lordosing and/or kyphosing of the legs can be carried out by the surgeon by means of suitable bending tools. If necessary, the legs may be cut so that the cut ends (which are then the free ends) overlie the next most caudal laminae below the fixation.

Elongated legs may be long enough to extend all the way or most of the way along the spine, and may be provided at or (preferably) near their ends remote from the loop with a crossbar (e.g., welded thereto) to maintain the legs parallel.

Three similar forms of device in accordance with the invention are preferably available, the only difference being the distance (or "waist") from the junction between the loop and the legs (or the "occipito-cervical angle") to the kinks (or the "hips"). With vertical migration of the odontoid peg the "high hips" device fits best, but one or other of the other two devices ("mid hips" or "low hips") usually fits all other patients. By tightening the sublaminae wires caudal to the "hips" a distraction can be obtained if this is indicated as desirable.

However, alternatively—or in addition—further kinks may be provided along the legs, whereby the legs can be secured to bones of the spine by sublaminae wires (or other strands) engaged with the further kinks.

The device (or devices) according to the invention may consist of stainless steel or titanium round rod e.g., of 3/16" or 4.7625 mm. diameter, bent to shape, but it may be feasible to mould similar devices using fibre reinforced plastics material, e.g., carbon-fibre reinforced polyester.

Three embodiments of the invention will now be described, by way of example only, with reference to the accompanying drawings, in which.

Figure 1:
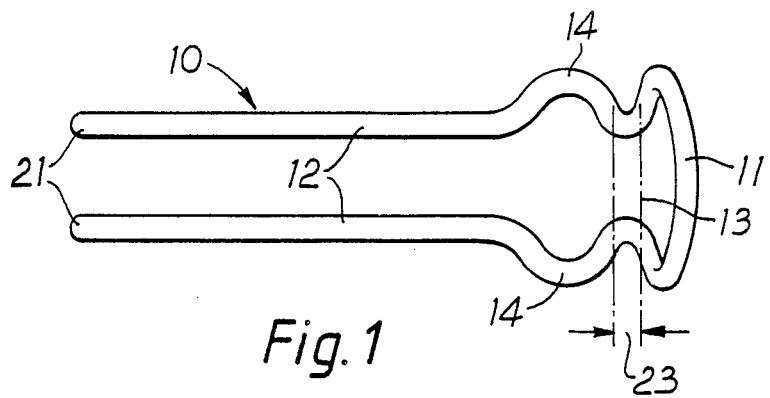
FIG. 1 is a plan view of a "high hips" device in accordance with the invention.
Figure 2:
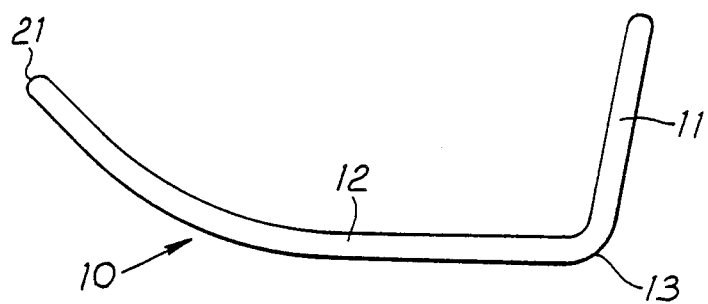
FIG. 2 is a side view of the device of FIG. 1.
Figure 3:
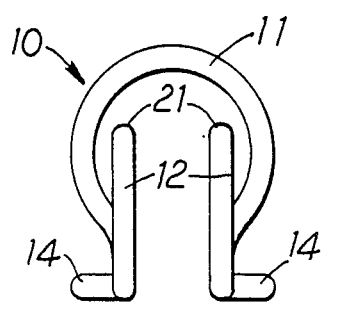
FIGS. 3 and 4 are end views of the device of FIGS. 1 and 2 as seen from the left and right hand ends respectively.
Figure 4:
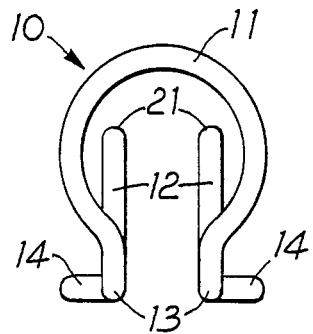
Figure 5:
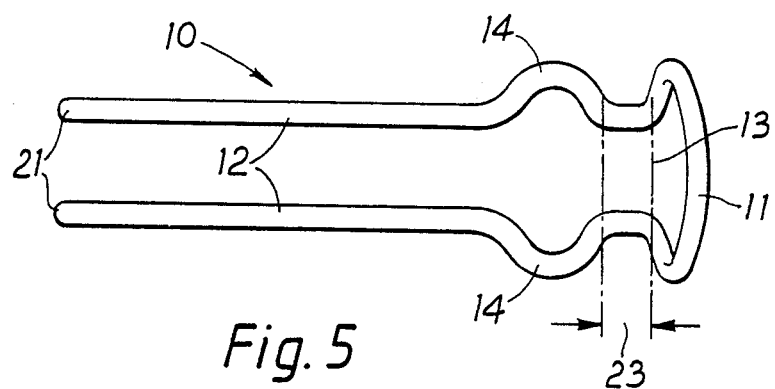
Figure 6:
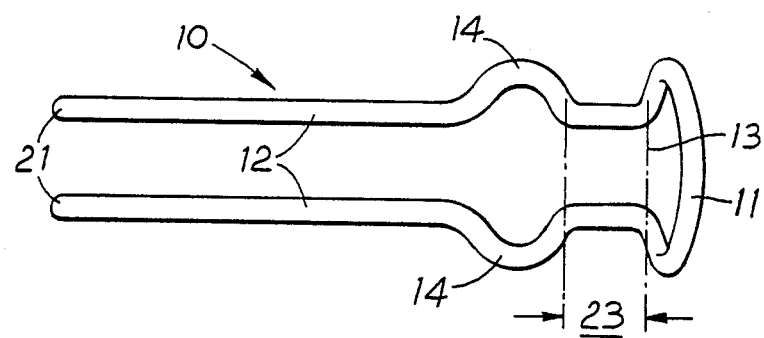
Figure 7:
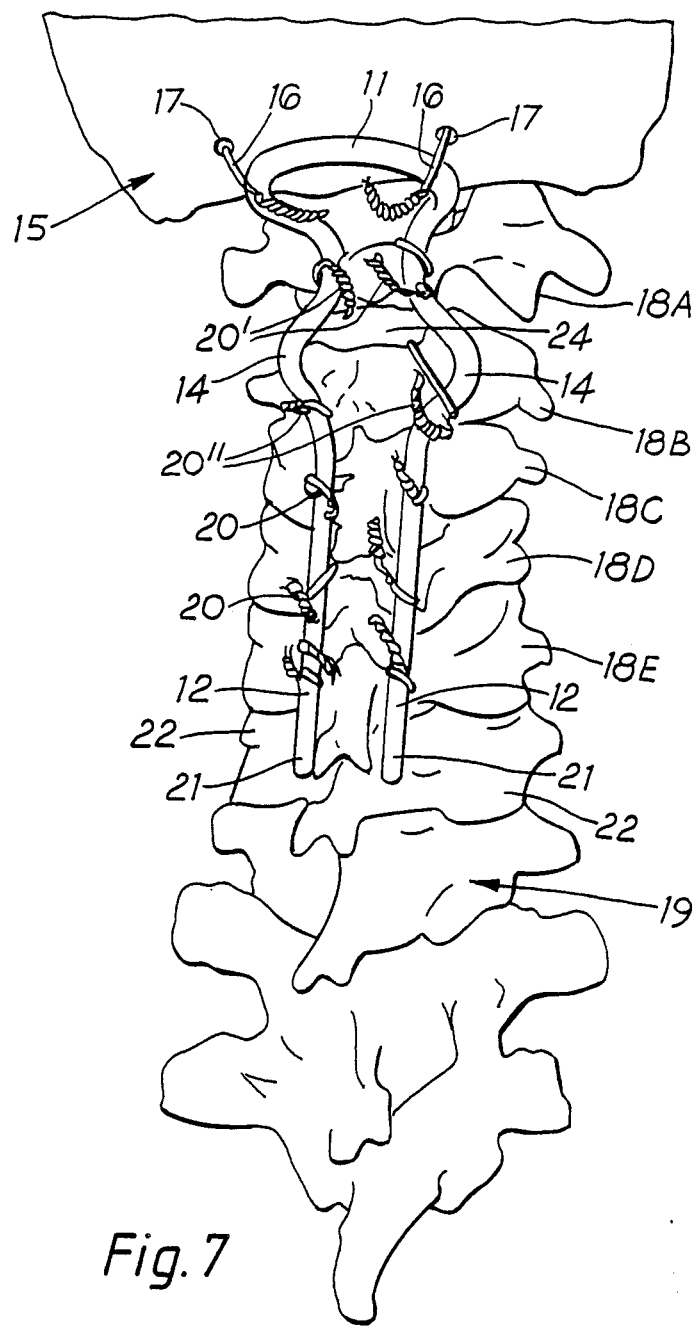
Figures 8, 9:
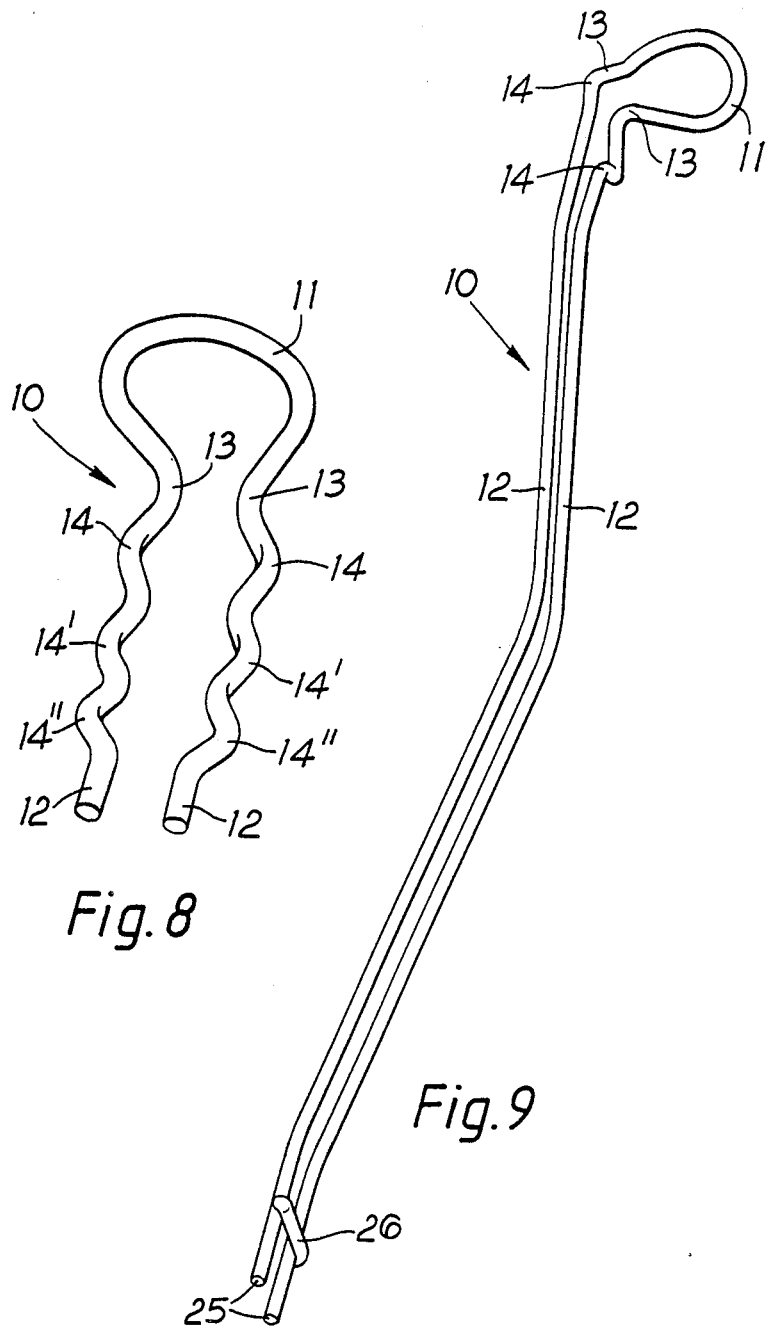

FIGS. 5 and 6 correspond to FIG. 1 but show, respectively, "mid hips" and "low hips" devices in accordance with the invention;

FIG. 7 is a perspective view illustrating the manner of use of the invention in respect of the "mid hips" device;

FIG. 8 is a perspective view of an alternative form of device in accordance with the invention having further kinks in the legs; and FIG. 9 is a perspective view of a further form of device in accordance with the invention having very elongated legs with a crossbar near the ends remote from the loop.

The device 10 shown in FIGS. 1 to 4 is intended for use in fixation of the skull to adjacent bones of the spine and comprises biocompatible rod-like material formed in a loop 11 of substantially circular form connecting a pair of generally parallel legs 12, with the loop and the legs at their junction 13 lying in planes that are generally perpendicular to each other, and the legs being provided adjacent that junction with outward kinks (or "hips") 14 whereby, when the loop 11 has been secured to the base of the skull 15 (see FIG. 7) by means of wires 16 through holes 17 in the skull and the legs 12 have been secured to adjacent bones 18A....18E of the spine 19 by sublaminae wires 20, wires 20' and 20" round the legs 12 at both sides of the "hips" 14 effect fixation of the skull in relation to the adjacent bones of the spine.

The loop 11 is formed in a flat plane, but can be bent by the surgeon, by means of suitable tools, to give it a superior concavity to fit the base of the skull 15. The neck should be extended to a normal alignment before testing the loop 11 for a good fit.

The legs 12 are formed towards their free ends 21 in a plane curving to the same side as that to which the loop 11 extends from the other ends of the legs, and appropriate lordosing and/or kyphosing of the legs can be carried out by the surgeon, by means of suitable bending tools, to achieve a normal cervical lordosis, which is essential for successful treatment. The legs 12 are elongated so as to be able to continue the fixation segmentally into the dorsal spine, and, if necessary, the legs are cut so that the cut ends (which are then the free ends 21) overlie the next most caudal laminae 22 below the fixation.

FIGS. 5 and 6 illustrate alternative forms of the device 10 in which the only difference is the distance (or "waist") 23 from the junction 13 (or the "occipito-cervical angle") to the "hips" 14. The device of FIG. 1 is the "high hips" device which fits best when there has been vertical migration of the odontoid peg 24, see FIG. 7, but bear in mind that this illustrates use of the "mid hips" device of FIG. 5, the device of FIG. 6 being the "low hips" embodiment.

In FIG. 8 further kinks 14' and 14" are provided in both legs 12, whereby the legs can be secured to bones of the spine by sublaminae wires (or other strands) engaged with the further kinks.

The further form of device shown in FIG. 9 has very elongated legs 12 long enough to extend all the way or most of the way along the spine, and the legs are provided near their ends 25 remote from the loop 11 with a crossbar 26 welded thereto to maintain the legs parallel.

What I claim is:

1. A device for fixation of a skull to bones of an adjacent spine comprising biocompatible rod-like material formed in the slope of a loop of substantially circular form terminating in and connecting a pair of generally parallel legs, with the loop and the legs at their junction lying in planes that are generally perpendicular to each other, and the legs being provided adjacent said junction with opposed kinks extending away from each other, whereby, when the loop has been secured to the base of the skull by means of wires passing through holes in the skull and the legs have been secured to bones of an adjacent spine by sublaminae wires, wires engaged round the legs at both sides of the kinks effect fixation of the skull in relation to the adjacent bones of the spine.

2. A device as in claim 1, wherein said substantially circular form constitutes a superior concavity to fit the base of the skull.

3. A device as in claim 1, said legs terminating in free ends remote from said loop, the legs being formed towards said free ends in a plane curving to the same side as that to which the loop extends from the other ends of the legs.

4. A device as in claim 1, wherein the legs are elongated so as to be able to continue the fixation segmentally into the dorsal spine.

5. A device as in claim 4, wherein said elongated legs are provided at or near said ends remote from the loop with a crossbar to maintain the legs parallel.

6. A device as in claim 1, including further kinks provided along the legs, whereby the legs can be secured to bones of the spine by sublaminae wires engaged with the further kinks.

7. A device as in claim 1, wherein said rod-like material consists of stainless steel or titanium round rod bent to shape.

8. A device as in claim 1, wherein said rod-like material is a mould from a fibre reinforced plastics material.

* * * * *

UNITED STATES PATENT AND TRADEMARK OFFICE
CERTIFICATE OF CORRECTION

PATENT NO. : 4,841,959
DATED : June 27, 1989
INVENTOR(S) : Andrew O. Ransford

It is certified that error appears in the above-indentified patent and that said Letters Patent is hereby corrected as shown below:

Column 1, Line 19 "in the slope of" should read
— in the shape of —

Column 3, Line 19 "in the slope of" should read
— in the shape of —

Signed and Sealed this

Nineteenth Day of April, 1994

Attest:

BRUCE LEHMAN

*Attesting Officer*        *Commissioner of Patents and Trademarks*